US007727537B2

(12) United States Patent
Modi

(10) Patent No.: US 7,727,537 B2
(45) **Date of Patent: *Jun. 1, 2010**

(54) STABILIZED COMPOSITIONS FOR TOPICAL ADMINISTRATION AND METHODS OF MAKING SAME

(75) Inventor: Pankaj Modi, Ancaster (CA)

(73) Assignee: DPM Therapeutics Corp., Burlington, ON (CA)

( * ) Notice: Subject to any disclaimer, the term of this patent is extended or adjusted under 35 U.S.C. 154(b) by 523 days.

This patent is subject to a terminal disclaimer.

(21) Appl. No.: 11/259,778

(22) Filed: Oct. 27, 2005

(65) Prior Publication Data

US 2006/0182794 A1 Aug. 17, 2006

Related U.S. Application Data

(63) Continuation-in-part of application No. 11/057,481, filed on Feb. 14, 2005.

(51) Int. Cl.

| | |
|---|---|
| *A61K 39/08* | (2006.01) |
| *A61K 31/74* | (2006.01) |
| *A61K 47/44* | (2006.01) |
| *A23J 1/00* | (2006.01) |

(52) U.S. Cl. .............. 424/239.1; 424/78.03; 424/284.1; 530/412

(58) Field of Classification Search ............... 424/239.1
See application file for complete search history.

(56) References Cited

U.S. PATENT DOCUMENTS

| | | | | |
|---|---|---|---|---|
| 5,728,391 | A | 3/1998 | Ikeya et al. | |
| 6,585,993 | B2 | 7/2003 | Donovan et al. | |
| 6,638,621 | B2 * | 10/2003 | Anderson | 428/402.24 |
| 6,689,349 | B1 | 2/2004 | Wohlrab et al. | |
| 6,756,045 | B1 | 6/2004 | Neudecker et al. | |
| 6,806,259 | B2 | 10/2004 | Udell et al. | |
| 6,998,113 | B1 * | 2/2006 | Traynor et al. | 424/59 |
| 2003/0118598 | A1 * | 6/2003 | Hunt | 424/184.1 |
| 2004/0033254 | A1 * | 2/2004 | Song et al. | 424/449 |
| 2004/0060569 | A1 | 4/2004 | Hanin | |
| 2004/0247623 | A1 | 12/2004 | Cady | |

FOREIGN PATENT DOCUMENTS

| | | | |
|---|---|---|---|
| DE | 198 05 827 A 1 | | 8/1999 |
| EP | 0319638 | A1 | 6/1989 |
| EP | 0525167 | B1 | 9/1995 |
| EP | 0812186 | B1 | 10/2001 |
| EP | 1 475 099 | A1 | 11/2004 |
| WO | WO9101719 | A1 | 2/1991 |
| WO | WO 01/58472 | | 8/2001 |
| WO | WO03015698 | A2 | 2/2003 |
| WO | WO 2004/060384 | A2 | 7/2004 |
| WO | WO2005046637 | A2 | 5/2005 |

OTHER PUBLICATIONS

Carpender et al., Interactions of Stabilizing Additives with Proteins During Freeze-Thawing and Freeze-Drying, International Symposium on Biological Product Freeze-Drying and Formulation, Oct. 24-26, 1990; Krager (1992), 225-239.

Goodnough et al., Stabilization of Botulinum Toxin Type A During Lyophilization, App & Envir. Micro. 58 (10) 3426-3428 (1992).

Schmidt, et al., Endoproteinase Activity of Type A Botulinum Neurotoxin Substrate Requirements and Activation by Serum Albumin, J. of Protein Chemistry, 16(1), 19-26 (1997).

* cited by examiner

*Primary Examiner*—Robert Mondesi
*Assistant Examiner*—Khatol Shahnan-Shah
(74) *Attorney, Agent, or Firm*—Gersten Savage LLP; James D. Fornari

(57) ABSTRACT

A stabilizing composition that also enhances permeation is provided for the topical or transdermal administration of an active ingredient. The composition preferably comprises collagen, elastin, sphingoside and cerebroside. Also provided are pharmaceutical or cosmetic formulations comprising an effective amount of an active agent and the stabilizing composition as well as methods of administering active agents topically or transdermally.

22 Claims, 4 Drawing Sheets

Western Blot Analysis #1

FIG. 2A

Lane-1 Molecular weight marker

Lane-3 Stabilized Botulinum Toxin (at time 0 month)

Western Blot Analysis (repeat # 2 at 6 months time)

FIG. 2B

Lane-1 Molecular weight marker
Lane- 2 Pure Botulinum Toxin (from vial)
Lane- 3 Stabilized Botulinum Toxin (6 months)

Molecular mass marker ranges from the top represents the molecular weights of 200, 116, 98, 67, 55, 37, 28 and 14 kDa.

Before and After Photographs (Botulinum Toxin Cream)

Before          After

FIG. 3A

Before          After

FIG. 3B

Before          After

FIG. 3C

Before          After

FIG. 3D

Before

After

STABILIZED COMPOSITIONS FOR TOPICAL ADMINISTRATION AND METHODS OF MAKING SAME

RELATED APPLICATIONS

This application is a continuation-in-part of application Ser. No. 11/057,481 filed on Feb. 14, 2005.

FIELD OF INVENTION

The present invention relates to methods for stabilizing active ingredients in pharmaceutical compositions to provide a prolonged shelf-life with enhanced availability of active ingredients.

BACKGROUND OF THE INVENTION

For storage stability and convenience of handling, pharmaceutical compositions are often formulated as a lyophilized or vacuum dried powder and stored at low temperatures between −10° C. to 4° C. The dry powder is typically reconstituted with a suitable fluid, such as saline or water, prior to administration to a patient. Alternatively, pharmaceutical composition can be formulated as an aqueous solution or suspension that includes a stabilizer to prevent degradation. However, many compounds are difficult to stabilize and there may be a loss of compound or activity during the formulation, reconstitution and/or the period storage. Stability problems can occur as a result of protein denaturation, degradation, dimerization, and/or polymerization. Various excipients have been used with differing degrees of success to try and stabilize an active agent in a pharmaceutical composition. Stabilizers may also be effective in reducing adhesion of the active agent to surfaces, such as the surfaces of laboratory glassware, vessels, the vial in which the pharmaceutical composition is reconstituted or the inside surface of a syringe used to inject the pharmaceutical composition. As well as being able to stabilize an active agent in a composition, an ideal stabilizing agent should have negligible immunogenicity when administered to a human patient.

It has proven particularly difficult to stabilize active agents for cosmetic or topical dermatological preparation. Various types of active agents are useful for the prophylaxis and treatment of cosmetic and dermatological skin changes, such as skin aging and, in particular, aging induced by oxidative or degenerative processes. It is also desirable to prepare preparations that can be administered topically to enhance wound healing or to treat painful neuropathies. Several problems have been encountered in trying to deliver active ingredients through the skin. The size of many active agents makes it difficult for them to penetrate through the skin and it has also proven difficult to stabilize some agents for storage at room temperature.

One example of an active agent that has been postulated to improve the appearance of skin lines is botulinum toxin Type A. However, pure botulinum toxin is extremely susceptible to denaturation due to surface denaturation, heat, and alkaline conditions. Inactivated toxin forms toxoid proteins which may be immunogenic and the resulting antibodies can render a patient refractory to the effects of the toxin. Furthermore, dilution of the toxin complex obtained by culturing, fermentation and purification processes to the much lower toxin concentrations used for a pharmaceutical composition results in rapid detoxification of the toxin unless a suitable stabilizing agent is present. Current formulations of botulinum toxin must be administered within four hours after reconstitution since the toxin molecule is very labile. During this time period, reconstituted botulinum toxin is stored in a refrigerator (4° C.). Breakdown of the toxin into toxoid can induce immune responses to the toxoid that can interfere with subsequent treatments. Current stabilizers that have been used in botulinum toxin formulations are animal derived albumin and gelatin. However, these stabilizers are not able to sufficiently stabilize botulinum toxin for storage at room temperature. Thus there was a specific need for a formulation that could enhance the stability of botulinum toxin and also promote its permeation through the skin.

Several efforts have been made to provide botulinum toxin formulations that can be stabilized and delivered in alternative ways. For example, U.S. Pat. No. 6,585,993 discloses a biocompatible implant for continuous release of a neurotoxin over a treatment period extending from one month to five years. While such an implantable system may be useful for certain situations, such as for the treatment of migraine, this type of implant system is not feasible for the treatment of facial, neck or hand wrinkles.

U.S. Patent Application No. 2004/0247623 suggests a method for the treatment of sensory neuron related distorters through transdermal application of a neurotoxin. This application is particularly directed to a method of treating migraine. The application suggests that botulinum toxin can be administered in a variety of ways.

International Patent Application WO 0158472 describes a pharmaceutical composition comprising botulinum toxin and a polysaccharide. This application teaches that the polysaccharide stabilizes the neurotoxin. However, other studies have shown that saccharides are poor stabilizers for botulinum toxin.

International Patent Application WO 04/060384 discloses a pharmaceutical botulinum toxin composition which includes a sequestration agent. The purpose of the sequestration agent is to prevent the diffusion of the botulinum toxin away from the site of injection. This does not address the need for stable compositions that can be applied to the surface of the skin.

While botulinum toxin can smooth out fine lines and wrinkles for most users, there are several disadvantages associated with its current use. The botulinum toxin must be administered in a doctor's office. The injections can be painful and there may be bruising. Adverse side effects occur in some injection treated patients. Most common side effects for treatment of frown line include droopy eyelids, nausea, flu-like symptoms (fever etc.), headache and respiratory infections. Less frequent reactions may include facial pain, redness at the injection site, and muscle weakness at other sites. Repeated treatments may lead to permanent paralysis of facial muscles leaving the face expressionless. Thus, there was a need for alternative methods of delivering botulinum toxin to the skin.

Another active agent that would be desirable to deliver through the skin is hyaluronic acid (HA). Hyaluronic acid is a naturally occurring high molecular weight polysaccharide that is found in many tissues of the body. Hyaluronic acid has been associated with maintaining moisture in the skin as well as with promoting wound healing and encouraging the formation of vessels. German Patent DE 19805827A describes the protective effect of hyaluronic acid on skin irritations. U.S. Pat. No. 5,728,391 also suggests the use of hyaluronic acid as an agent for treating skin disease. Various formulations for the oral delivery of HA have been suggested. To enhance the effect of HA on the skin, it is desirable to formulate a composition that can be applied topically to the skin. One of the difficulties, however, in trying to increase the permeation of HA in the skin is the size of the molecule. The large polymeric structure that gives HA its beneficial effects also makes it difficult to acquire from outside the body. Thus, there was an unmet need for improved formulations of HA that can be applied topically.

The process that leads to skin aging and wrinkles is complex. A primary cause of wrinkling is a build-up of free radical toxic plaque that binds to collagen and elastin fibers, causing the skin's supportive structure to become inflexible and unhealthy. Laugh lines, smile lines, crow's feet or facial creases appear in areas where repeated muscle movement occurs. Thus, it would be desirable to be able to deliver free radical scavengers to the skin.

Botulinum toxin, hyaluronic acid and anti-oxidants are just a few examples of active agents that it is desirable to deliver to the skin. Other active agents may include enzyme inhibitors, vasodilaters, perflourocarbons, hormones, growth factors, vaccines, drugs, small molecules, amines, peroxides, analgesics and other therapeutic agents. Agents which promote wound healing or reduce pain are also active agents that it would be desirable to administer through the skin.

Thus, there was a need for newer methods for stabilization of active agents for the preparation of topical and cosmetic preparation. There was also a need for improved systems for delivery of active agents to the skin. The present invention addresses those needs.

SUMMARY OF THE INVENTION

The present invention addresses the need for improved dermatological delivery of active agents by providing a method for stabilizing active agents for storage at room temperature and for enhancing the permeation of the active ingredients into the skin. The invention also provides compositions prepared using the method for the topical delivery of at least one active agent.

In one aspect of the invention, the method comprises encapsulating an active agent in a phospholipid micelle-like coating. The active agent is then admixed with a solution containing collagen and/or elastin.

In another aspect of the invention, a composition for topical delivery of at least one active agent is provided. The composition comprises the active agent in a phospholipid micelle, collagen and an acceptable carrier. The composition also optionally includes elastin, preferably low molecular weight cross-linked elastin.

In one preferred embodiment, the active agent is selected from the group consisting of a muscle paralyzing agent, hyaluronic acid, Vitamin A, Vitamin C, Vitamin E, Zinc, Selenium, lycopene, N-Acetyl-Cysteine, natural plant extracts of Grape Skin, Bilberry and Green Tea, vasodilators, hormones, growth factors, enzyme inhibitors, vaccine agents, drugs, therapeutic proteins, small molecules, antiperspirant agents, amines, peroxides, analgesics and combinations thereof.

Preferred phospholipids include sphingosine and cerebroside. In a preferred embodiment, the micelle comprises both sphingosine and cerebroside. In one particular embodiment, the sphingosine and cerebroside are combined in equal amounts.

In another preferred embodiment, the composition of the present invention further comprises an absorption enhancer. The enhancer may be selected from the group consisting of d-limonene, allantoin, fulvic acid, myrrh, hydroquinone glyquin, quillaja saponaria (QTS), and acanthophyllum squarrusom (ATS).

In a further preferred embodiment, the composition is formulated in a format selected from the group consisting of a cream, a lotion, a spray, an ointment, a gel, a powdered mask, a paste, a cleanser, and a foundation.

The composition may optionally include an additive selected from the group consisting of a perfume, colorant, thickening agent, vegetable oil, emulsifier, solvent, pH adjusting agent, antiseptic agent, preservative, vitamin, sunblock, surfactants and combinations thereof.

In a preferred embodiment, the present invention provides a composition comprising:
 approximately 1 to 40% w/w collagen;
 approximately 1 to 40% w/w elastin;
 approximately 0.1 to 15% sphingoside phospholipid; and
 approximately 0.1 to 15% cerebroside phospholipid.

In another aspect, the present invention provides a method for making a stabilized active agent composition. The method comprises the steps of:
 i. preparing a phQspholipid solution comprising a phospholipid in a solvent;
 ii. admixing the phospholipid solution with an active agent so as provide a phospholipid micelle encapsulated active agent solution; and
 iii. combining the micelle solution with a solution of solubilized collagen and elastin.

In a preferred embodiment of the method, the phospholipid is selected from the group consisting of sphingosine, cerebroside and combinations thereof. More preferably, sphingosine and cerebroside are used in equal amounts.

In a further preferred embodiment, the solvent used is an alcohol. Preferred alcohols include isopropanol, ethanol and mixtures thereof.

In another preferred embodiment, the solution of solubilized collagen and elastin comprises equal amounts of collagen and elastin.

Active agents that can be used in the method of the invention include botulinum toxin, hyaluronic acid, Vitamin A, Vitamin C, Vitamin E, Zinc, Selenium, lycopene, N-Acetyl-Cysteine, natural plant extracts of Grape Skin, Bilberry and Green Tea, vasodilators, hormones, growth factors, vaccine agents, drugs, therapeutic proteins, small molecules, antiperspirant agents, analgesics and combinations thereof. Preferred active agents for use in the method are hyaluronic acid and/or botulinum toxin.

The method of the present invention may include the further step of adding a permeation enhancing compound. The enhancing compound is preferably selected from the group consisting of d-limonene, allantoin, fulvic acid, myrrh, hydroquinone glyquin, quillaja saponaria, and acanthophyllum squarrusom.

In a preferred method of the invention, about 0.1 to 15 wt/wt % of sphingosine and about 0.1 to 15 wt/wt % of cerebroside are used to form the micellar coating.

In a further preferred method, additional ingredients are added to form a cream, lotion, gel, ointment, or spray.

In a further aspect of the invention, a method of treating skin is provided. The method comprises applying the composition described above daily to areas of the skin which are wrinkled or damaged.

The present invention addresses many of the problems of the prior art. For example, botulinum toxin and other active agents can be delivered without painful injections. The compositions of the present invention can be safely used in areas such as the throat and neck, around the mouth, near the eye and on the hands. The compositions can be formulated as a cream or lotion and can be stored at room temperature for extended periods of time without any loss of activity of the active ingredient. An advantage of the method of the present invention is that it eliminates the need for the use of blood derived products as a stabilizing agents. In addition, the methods and compositions of the present invention are cost effective and simple to use. Rather than one single large dose being delivered once to a single site, the methods and compositions of the present invention allow the active agent to be administered at low dose, daily, to provide an effective treatment with enhanced safety and reduced side effects.

Certain compositions of the invention are useful to reduce fine lines and wrinkles, increase the moisture level of the skin, increase skin elasticity and resilience, increase the firmness of the skin, improve skin tone, texture and overall radiance, diminish bags under the eyes, rejuvenate the skin, prevent damage from chemical stress, protect the skin from UV rays and free-radical damage, promote wound healing and remove irregular pigmentation. Specific compositions of the invention may be useful to treat pain.

BRIEF DESCRIPTION OF THE DRAWINGS

These and other features of the invention will become more apparent from the following description in which reference is made to the appended drawings wherein:

FIGS. 2A and 2B illustrate representative Western Blot analyses of the botulinum toxin composition of the invention;

FIGS. 3A to 3D are photographs of patients treated with the botulinum toxin composition of the present invention;

DETAILED DESCRIPTION

Figure 1:
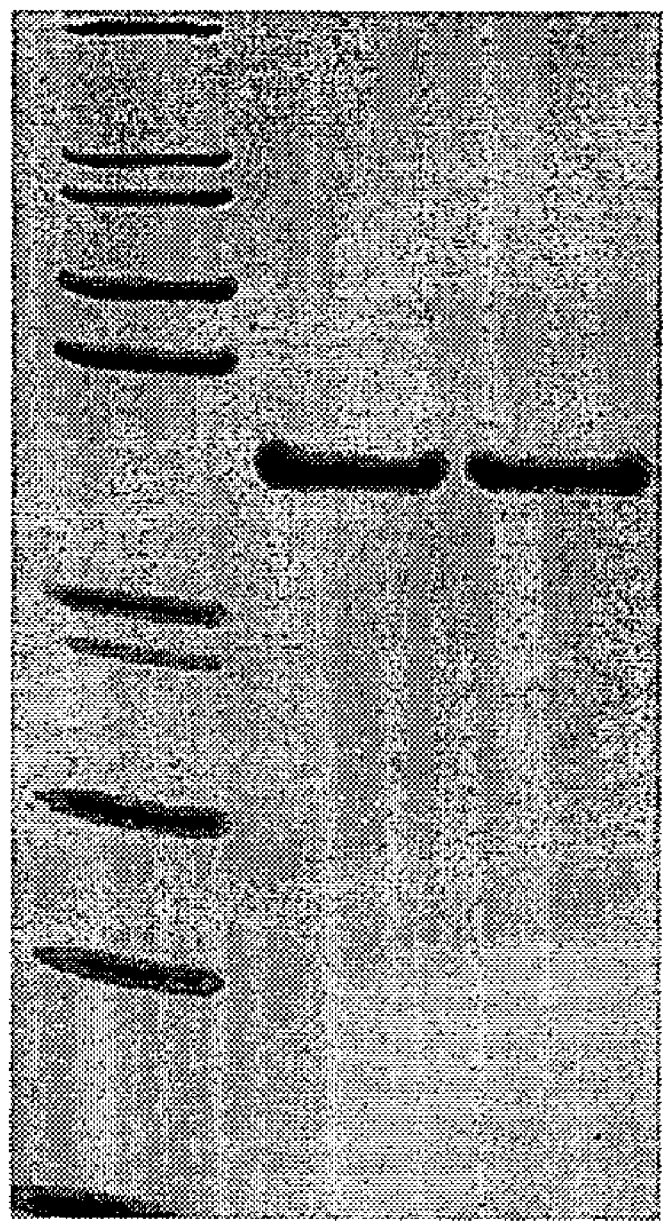
FIG. 1 illustrates an SDS polyacrylamide gel analysis of stabilized botulinum toxin.

The present invention provides methods of preparing a pharmaceutical or cosmetic composition for enhanced topical delivery of at least one active agent and compositions prepared by the methods.

The method of the invention comprises encapsulating an active agent in a phospholipid micelle. The micelle solution is then preferably combined with a base composition that includes collagen. Briefly, the phospholipid is dissolved in a suitable solvent, such as an alcohol. For example, the phospholipid may be dissolved in ethanol or a mixture of ethanol and isopropanol. The alcohol is removed by, for example, rotary vacuum evaporation. An aqueous solution containing the active agent is then added. The active agent thus becomes encapsulated by a phospholipid micelle structure. This solution can then be combined with a base solution comprising collagen. It has also been found to be advantageous to include elastin, especially cross-linked low molecular weight elastin, in the base composition.

Collagen can act as a stabilizer. In addition, collagen helps improve the tissue's underlying foundation and contributes to hydration. Collagen is able to penetrate the skin without the aid of any penetration enhancers.

In a preferred method of the invention, elastin is also included. Low-molecular weigh elastin is able-to penetrate the skin without the aid of any penetration enhancers. Collagen and low molecular weight soluble elastin complex in conjunction with a skin-enhancing active agent, such as botulinum toxin or hyaluronic acid, help diminish the appearance of wrinkles.

While various types of phospholipids can be used to form the micelles, a sphingoside is one preferred phospholipid. Sphingolipid or sphingosine-1-phosphate has been recognized as a bioactive molecule involved in the regulation of cell growth, differentiation, survival, and chemotaxis as well as angiogenesis and embryogenesis. Other species of ceramides or sphingolipids such as (N-acyl-sphingosine) and dihydroceramide (N-acyl sphinganine) are also useful in the present invention. Galactosylceramide (cerebroside), a metabolite of sphingolipids is also a preferred phospholipid. Cerebroside is a myelin related protein that plays an important role in the regulation of cell growth, differentiation, survival, and chemotaxis. Cerebroside sulfates are important membrane constituents. Both sphingosine and cerebroside have been found to be excellent phospholipids for use in the method of the present invention. While either of these phospholipids can be used alone, combinations of sphingosine and cerebroside are particularly effective. When used in equal amounts, sphingosine and cerebroside form a micelle structure that provides a very effective vehicle for delivery of active agents. Other phospholipids, such as phosphatidyl choline or phosphatidyl serine are also highly effective, either alone or in combination. Other phospholipids that can form a micellar structure are also useful in the invention.

According to one preferred method of the invention, a stabilized composition is made by combining equal amounts of collagen and low molecular weight elastin in a solvent, such as saline. In a separate flask, equal amounts of sphingosine and cerebroside are dissolved in an alcohol, preferably ethanol. The alcohol is then removed by rotary vacuum evaporation. This results in a coating of sphingosine and cerebroside on the flask. A solution containing the active agent is added to the flask. This results in the formation of micelles of sphingosine, cerebroside and active agent. This micellar composition is added to the mixture of collagen and elastin and stirred. This composition can then be stored at room temperature.

In another preferred embodiment, the composition comprises about 1 to 40% w/w collagen, 1 to 40% w/w elastin, 0.1 to 15% w/w sphingosine and 0.1 to 15% w/w cerebroside and the active agent.

Additional components which enhance stability or facilitate absorption/penetration may also be included. Further additional components can be included to formulate the composition into a format, such as a cream, lotion, spray, mask, gel, etc., that is suitable for topical administration. Ingredients that improve the desirability of the composition such as dyes, fragrances, emollients, etc. are optionally included. The composition may also be included in make-up formulations such as foundations or lip balm.

Stabilizers that help to preserve or maintain the biological structure (i.e. the three dimensional conformation) and/or the biological activity of an active agent can be included. Stabilizers can be proteins or polysaccharides. Examples of protein stabilizers include hydroxyethyl starch (hetastarch), gelatin, collagen, or collagen. The primary stabilizer can be a synthetic agent that does not induce an immune response or induces an attenuated immune response in a subject. Additional stabilizers may also be included in a composition. These additional or secondary stabilizers may be used alone or in combination with primary stabilizers. Exemplary secondary stabilizers include, but are not limited to non-oxidizing amino acid derivatives (such as a tryptophan derivate, such as Nacetyl-fryptophan ("NAT")), caprylate (i.e. sodium caprylate), a polysorbate (i.e. P80), amino acids, and divalent metal cations such as zinc. A composition can also include preservative agents such as benzyl alcohol, benzoic acid, phenol, parabens and sorbic acid or a cresol, such as an M-cresol.

Enhancing agents that promote the absorption of an active agent by the skin may also be included in the compositions of the invention. Examples of enhancing agents include, but are not limited to, alcohols, such as short chain alcohols, long chain alcohols, or polyalcohols, amines and amides, such as urea, amino acids or their esters, amides, AZONE(R)), derivatives of AZONE(R), pyrrolidones, or derivatives of pyrrolidones; terpenes and derivatives of terpenes; fatty acids and their esters; macrocyclic compounds; tensides; or sulfoxides such as, decylmethylsulfoxide. Liposomes, transfersomes, lecithin vesicles, ethosomes, water surfactants, such as anionic, cationic, and nonionic surfactants, polyols, and essential oils can also function as enhancing agents.

In one embodiment of the invention, d-limonene is included in the composition to enhance penetration of an active agent through the dermal layer. Limonene was found to be an effective enhancer at 0.30%, enhancing skin permeation of botulinum toxin Type A approximately fourfold.

In another preferred embodiment of the invention, allantoin is included in the preparation. Allantoin acts as a skin protectant and a mild neutral permeation enhancer.

In another preferred embodiment, fulvic acid is included in the preparation. Fulvic acid is a low molecular weight antioxidant that enhances the body's absorption of drugs through the transdermal route without any side effects.

Myrrh is a further optional ingredient in the skin cream preparation of the invention. Myrrh is a gum resin extracted from Arabian and Somolian shrubs that helps soothe inflamed tissues and rejuvenate skin, hair, and nails.

Eldopaque or hydroquinone glyquin may also be included. It is used to lighten the dark colored patches of skin caused by birth control pills, hormone medicine, injury to the skin, or simply aging. It may be included together with sunscreen to help prevent these spots from reoccurring due to sunlight or UV light exposure.

Quillaja saponaria (QTS) and Acanthophyllum squarrusom (ATS) total saponins are two natural enhancers that may also be included in a composition of the invention. They demonstrate moderate activity as skin penetration enhancers.

The enhancing agents may be included at various stages of the process. For example, they may be added to the stabilized composition at the same time as the micellar composition is added to the collagen and elastin mixture. Preferably, the enhancing compounds are introduced during the formulation of the stabilized composition into a pharmaceutical or cosmetic formulation. The preparation of an exemplary formulation for topical application is described in Example 3 below.

Topical compositions prepared according to the methods of the invention provide effective systems for dermatological delivery of active agents. In one aspect, the present invention provides a composition for preferred delivery of botulinum toxin. Botulinum toxin Type A, Type B, Type C, Type D, Type E, Type F, and/or Type G can be formulated according to the method of the invention into a composition for topical delivery. The method of the present invention based on the use of collage in combination with elastin-binding protein (EBP) and mixture of sphingosine and cerebroside maintains the integrity of the complex without denaturing or fragmentation or detoxification. Thus, botulinum toxin can be stabilized using the methods of present invention and the stabilized toxin can be successfully delivered transdermally to achieve similar results to those obtained by intramuscular injection of botulinum toxin. The formulation can be applied all over the face and neck and hands as opposed to a botulinum toxin injection which is targeted primarily to areas around eyes and the forehead to reduce the wrinkle. A further advantage is that proteins like collagen, elastin and sphingomyelins are non-immunogenic.

A preferred method for preparing a stabilized botulinum toxin composition for topical application is described in Example 1 below. The method of the present invention was used to stabilize botulinum toxin A in a cream format suitable for application to the skin. Briefly, equal amounts of collagen and elastin are solubilized in saline. In a separate flask, equal amounts of sphingosine and cerebroside are dissolved in alcohol. The alcohol is then removed. Botulinum toxin A is dissolved in saline and is then added to the flask and the flask is swirled to coat the botulinum toxin protein with a phospholipid micelle coating. This solution is then added to the solution of collagen and elastin. FIGS. 1 and 2 illustrate SDS-PAGE and Western blots of compositions of stabilized botulinum toxin. It is clearly apparent that this method can be used to prepare compositions having other types of botulinum toxin.

The present invention provides a composition that is capable of delivering a botulinum toxin through a person's skin. The composition contains an enhancing agent that facilitates the permeation of the botulinum toxin through the patient's skin. The composition is suitable for topical administration in a format whereby the composition penetrates the skin and transdermally denervates an underlying muscle. The composition may also be provided on a patch that is adhesively secured to the skin so that the toxin can pass from the patch through the skin to denervate an underlying muscle. Compositions containing botulinum toxin and an enhancing agent can be used to successfully treat several types of disorders associate with neurotransmitter release when applied to a person's skin. Examples of disorders amenable to treatment by the topical administration of the compositions set forth herein include, and are not limited to, wrinkles, such as brow furrows, headaches, such as migraine, headache pain, cervical dystonia, focal hand dystonia, neurogenic inflammation, hyperhydrosis, belpharospasm, strabismus, hemifacial spasm, eyelid disorder, cerebral palsy, focal spasticity, limb spasticity, tics, tremors, bruxism, anal fissure, fibromyalgia, dysphagia, lacrimation, and pain from muscle spasms. The compositions disclosed herein provide localized relief via delivery of botulinum toxin.

Figure 4:
FIG. 4 is a series of photographs of patients treated with the HA composition of the present invention.
Figure 4:
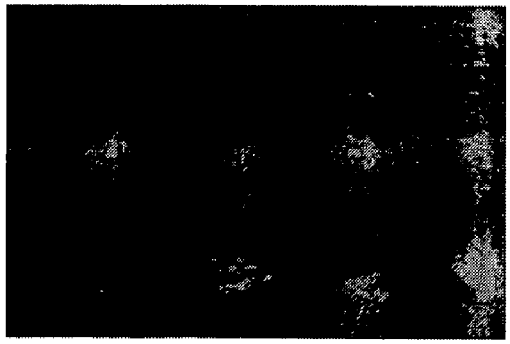
Figure 4:
Figure 4:
Figure 4:
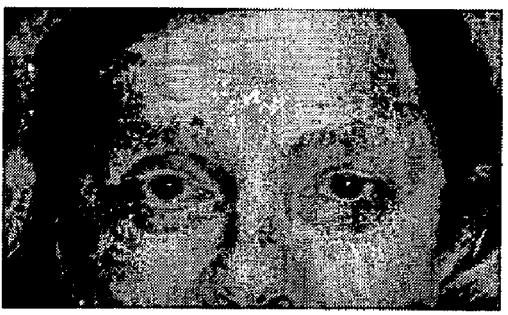
Figure 4:

The compositions and formulations of the invention are useful to reduce the signs of aging. Clinical trials were conducted using a topical cream formulation containing botulinum toxin. Details of the trial can be found in Example 4 below. As can be clearly seen from the before and after photographs in FIG. 3, topical administration of stabilized botulinum toxin cream significantly reduces the signs of aging. The effects of a composition comprising hyaluronic acid on the signs of aging were also assessed. As shown in FIG. 4, the hyaluronic acid composition was highly effective.

In another aspect of the invention, a pharmaceutical or cosmetic formulation is provided containing an effective amount of an active agent and an effective amount of the stabilizing enhancing composition, and a pharmaceutically acceptable carrier suitable for topical or transdermal administration. The formulation may be in any form suitable for application to the skin. For example, it may take the form of a cream, a lotion, a gel, an ointment, a paste, or a solution. The formulation may include lipozone, micelles, or microspheres. The formulation may be a cosmetic composition that includes in addition to the stabilizers and the active ingredients water and other additives that are normally used in cosmetics. For example, it may include thickening agents, preservatives, emulsifiers, perfumes, dyes or coloring, vegetable or mineral oil, antiseptic agents, acidifying or alkalizing agents, vitamins, anti-UV agents, surfactant, solvents, pH stabilizing agents, and other active ingredients known to be effective on the skin. The cosmetic composition may also be provided as skin foundation, lip balm, etc.

The methods of the present invention can also be used to prepare compositions for the topical delivery of hyaluronic acid. Details of a preferred method of preparing a composition comprising hyaluronic acid can be found in Example 6 below. Briefly, equal amounts of collagen and elastin are solubilized in saline. In a separate flask, equal amounts of sphingosine or phosphatidyl choline and cerebroside or phosphatidyl serine are dissolved in alcohol. The alcohol is then removed. Hyaluronic acid or sodium hyaluronate solution is then added to the flask arid the flask is swirled to coat the active agent. This solution is then added to the solution of collagen and elastin. Photographs illustrating the effects of treatment with this composition are shown in FIG. 4. In this composition, collagen and elastin are included as optional components to enhance skin healing.

Other skin enhancing active agents which can delivered via the methods and compositions of the present invention include various types of anti-oxidants. Some examples of free radical scavengers that maybe included in compositions of the invention include, but are not limited to, Vitamins A, C and E, the minerals Zinc and Selenium, lycopene, the amino acid N-Acetyl-Cysteine and natural plant extracts of Grape Skin, Bilberry and Green Tea.

In another aspect of the invention, the delivery system of the present invention can be used to deliver agents that promote healing. For example, vasodilators, such as nitroglycerin and glycerin mononitrate can be encapsulated in a phospholipid micelle and then combined with collagen and/or elastin in a lotion or cream formulation and applied to the skin. Without being limited by the explanation, it is thought that the formulation of vasodilators in a topical composition according to the invention enhances the rate of penetration as compared to administration via, for example, a skin patch. Inclusion of hydrogen peroxide and/or a perfluorocarbon may further enhance oxygenation and healing.

The methods of the invention have been demonstrated to be useful for the formulation of very different agents, e.g. botulinum toxin and HA. It is reasonable to conclude that the methods and compositions of the present invention can also be used to efficiently deliver other active agents to the skin. Examples of other active agents include other muscle paralysing agents, hormones, growth factors, vaccine agents, drugs, therapeutic proteins, small molecules and antiperspirant agents. The methods of the present invention can also be used to formulate compositions for the treatment of pain, comprising as the active agent, analgesics.

Examples of further active agents that can be delivered in compositions of the invention include, but are not limited to androgens, androstenediol and androisoxazole (for anabolic disorders), testosterone (hypogonadism, muscle wasting, male impotence, postmenopausal symptoms in women), dehydrotestosterdne (hypogdnadism, muscle wasting), dehydroepiandrostenone (muscle wasting, fat reduction, fitness); estrogens (postmenopausal symptoms, birth control), 17 betaestradiol, estradiol-3, 17-diacetate, estradiol-3 -acetate, estradiol-17-acetate, estradiol-3, 17-valerate, estradiol-3 -valerate, estradiol-17-valerate, ethinyl estradiol, estrone; progesterones (prevent endometriosis, prevent endometrial cancer, control habitual abortion, suppress or synchronize estrus, promote hair growth), progesterone (preg-4-ene-3 ,20-dione), norethindrone, norgestrieone, norgestadienone, norgestrel, norgestimate, progestogenic acid, dihydroprogesterol, nomagesterol. The testosterone hormone may be used in any of its usual forms, such as, acetate, propionate, 17-beta-cyclopentanepropionate, enanthanate, isobutyrate, undeconate, and the like. Similarly, the estradiols may additionally be used in any of the known or newly developed forms, such as, for example, pivalate, propionate, cypionate, benzoate and other esters. Other drugs such as insulin, insulin like growth factors, vaccines, peptides like; GLP, IGF, heparin, hirugen, hirulos, huridine, mumps, measles and rubella vaccine, typhoid vaccine, hepatitis A vaccine, hepatitis B vaccine, herpes simplex virus, bacterial toxoids, cholera toxin B-subunit, influenza vaccine virus, bordetala pertussis, vaccinia virus, adenovirus, canary pox, polio vaccine virus, *plasmodium falciparum*, *bacillus* calmette geurin (BCG), *klebsiella pneumoniae*, HIV envelop glycoproteins, bovine somatropine, estrogens, androgens, insulin growth factors, interleukin-l, interleukin-Il and cytokins, small molecule drugs such as NSAJD, narcotics, etc. may be delivered using the compositions of the present invention.

The compositions of the present invention may contain a single active agent or multiple active agents in the same composition. For example, a composition for topical delivery may comprise micelle encapsulated botulinum toxin or hyaluronic acid or both. Various combinations of active agents are contemplated for inclusion in the compositions of the invention.

The present invention has been described with regard to one or more embodiments. However, it will be apparent to persons skilled in the art that a number of variations and modifications can be made without departing from the scope of the invention as defined in the claims.

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

EXAMPLES

The examples are described for the purposes of illustration and are not intended to limit the scope of the invention.

Example 1

Preparations of Botulinum Toxin Compositions

Botulinum toxin (BOTOX™) vials were reconstituted of sterile saline solution (0.9%). The vials were shaken vigorously to dissolve the botulinum toxin. The reconstituted vials were kept refrigerated and were utilized within 1 hour of reconstitution.

In a round bottom flask of 50 mL capacity, 10 mg of soluble collagen and 10 mg of elastin were combined. .The mixture was solubilized in 10 mL of sterile saline solution (0.9%) with continuous stirring. In a separate 50 mL round bottom flask, 5 mg of sphingosine and 5 mg cerebroside were combined. This mixture was dissolved in pure ethanol. The alcohol was completely removed by rotary vacuum evaporation to obtain a uniform coating of the sphingosine and cerebroside on the flask wall. To this flask 800 units of botulinum toxin solution in 6 ml of (0.9%) saline was added. The flask was swirled and then stirred continuously for 5 minutes at room temperature to uniformly coat the botulinum toxin with the sphingosine and cerebroside micelle coating. This coated and preserved micellar botulinum toxin solution was then added to the flask containing the mixture of collagen and cross-linked, low molecular weight elastin. The solution was stirred for about 5 minutes and then kept at room temperature in a brown glass vial.

Example 2

SDS-PAGE and Western Blot Analysis

The stability of the preserved botulinum toxin solution was analyzed by standard analytical techniques using SDS-PAGE and Western Blot analysis and HPLC analysis at time zero (few minutes after the preparation of the coated stabilized solution) and thereafter every month. The preparation was compared with uncoated botulinum toxin solution.

SDS-PAGE was performed inmall cases under reducing conditions with a BioRad Mini-cell apparatus (BioRad, Calif.) with 10% precast tricine gels. Freshly diluted botulinum toxin (pure sample diluted with saline) was loaded in one lane and the stabilized botulinum toxin was loaded in a second lane. Both lanes were loaded with approximately 100 units of the toxin. The loading buffer, tank buffer, and the molecular weight markers were obtained from BioRad Laboratories. The protein bands were visualized by the Coomassie blue staining technique. Protein concentration (density) from SDS polyacrylamide gels was measured with a BioRad densitometry system and analyzed with the standard imaging software analyzer. The comparison of the Botulinum toxin A bands, i.e. the neat botulinum toxin without stabilization and the stabilized botulinum toxin revealed no degradation in the stabilized botulinum toxin which was kept at a room temperature for 6 months. The results are shown in FIG. 1.

Western Blot Analysis

For Western blot analysis, proteins separated on SDS-polyacrylamide gels were transferred to nitrocellulose membranes at 25 V for 60 mm using a BioRad protein blot module. After the complete transfer of the protein from the gel, the protein binding sites on the membranes were blocked by incubation at room temperature in 5% skim milk-Tris-buffered saline (TBS) for 60 mm. Membranes were then incubated at a room temperature with affinity-purified MAb produced against the botulinum toxin at 5 µg/ml in 5% skim milk-TBS for 4 hrs. After several washes with TBS buffer, the membranes were incubated at room temperature with affinity-purified goat anti-mouse IgG (Sigma) at 4 µg/ml in 5% skim milk-TBS buffer for 3 hrs. After another four to five washes with the TBS buffer, the membranes were incubated with TMB [3,3',5,5'-tetramethylbenzidine] membrane substrate (BioRad Laboratories) until color developed. This analysis revealed that after 6 months the botulinum toxin at room temperature was stable and was not degraded or denatured. The results of two exemplary Western Blots are shown in FIGS. 2A and 2B.

Example 3

Botulinum Toxin Cream Formulation

The stabilized botulinumitoxin composition was formulated into a cream for topical administration as outlined below.

| Total Volume of the cream (400 mL) | |
|---|---|
| Phase A: | |
| De-ionized Water | 74.7% |
| Tetra Sodium EDTA | 0.5-0.7% |
| Methyl Paraben | 0.2% |
| Propylene Glycol | 3.0%-4.0% |
| Glycerin | 3.0%-4.0% |
| Phase B: | |
| Cetyl Alcohol (Ado 1 52 NE) | 2.0% |
| Cetearyl Alcohol | 2.0% |
| Glyceryl Stearate | 2.0% |
| PEG-100 Stearate | 1-2% |
| Stearic Acid (Emersol 132) | 4.5% |
| Sorbitan Palmitate | 0.5-0.7% |
| Polysorbate-85 | 1.0% |
| Polysorbate 60 | 0.5-1% |
| Lanolin Alcohol (Ritachol) | 1.0% |
| HoHoba Oil | 0.5-1% |
| Lanolin | 1-2% |
| Tocopheryl Acetate | 0.5-1% |
| Dimethicone 200 | 0.7-1.0% |
| BHA | 0.1% |
| Propylparaben | 0.1% |
| Diazolidinyl UREA | 0.2% |
| Phase C: | |
| Fragrance (lilac, jasmine) | as needed |
| Aloe Vera (powder) | 1.5%-2.0% |
| CoQ-10 | 0.5% |
| Retinyl A | 0.03-0.05% |
| Hyaluronic Acid (pure) | 1.0-1.5% |
| Talcum Powder (Ti02) | 1.0-1.5% |
| Phase D: | |
| d-limonene | 0.7% |
| Allantoin | 0.5% |
| Fulvic Acid | 0.5% |
| Quillaja saponaria (QTS) | 0.3% |
| Acanthophyllum squaimsom (ATS) | 0.3% |
| Myrrh Extract | 0.2% |
| Hydroquinone Glyquin | 4.0% |
| Phase E: | |
| Stabilized Botulinum Toxin in Collagen Matrix | 800 units |

Procedure:

Heat Phase A and Phase B separately with agitation to 75 C. Add Phase A to Phase B and mix 30 minutes at 75 C. Cool down to 20-22 C and then add Phase C, D and E and continue to agitate until homogenous and one phase.

Example 4

Clinical Studies in Human Subjects

The effectiveness of the stabilized botulinum toxin (Botox) was tested using a cream formulation. Human subjects with wrinkles applied the cream for a period of month or more. The subjects were photographed before and after one month of the application of the cream on their face.

Botulinum toxin Type A was not present in the peripheral blood at measurable levels following the dermal application of the cream at the low doses of 1.7 units per mL of the cream. Each cream vial contained 50 units of Botulinum toxin in 30 ml of cream. The recommended quantities of neurotoxin administered at each treatment (in the morning and at the bed time) did not result in systemic, adverse clinical effects, i.e. muscle weakness, in patients without other neuromuscular dysfunction.

Example 5

Clinical Studies: Assessment of the Glabellar Lines

A randomized, single-center, double blind, placebo-controlled (placebo cream contained all the ingredients except the Botulinum toxin), parallel-group study was conducted to evaluate the effectiveness of the stabilized Botulinum toxin cream of the invention for use in the temporary improvement of the appearance of moderate to severe Glabellar facial lines. The study enrolled 40 healthy adult patients (ages 40 to 75 years, female or male) with Glabellar lines of at least moderate severity at maximum frown. Patients were excluded if they had an infection or skin problems, history of facial nerve palsy, marked facial asymmetry, ptosis, excessive dermatochalasis, deep dermal scarring, thick sebaceous skin, inability to substantially lessen glabellar lines even by physically spreading them apart or had a known history of neuromuscular disorder or other disorder that could interfere with neuromuscular function. Subjects were asked to apply the cream twice a day, once in the morning and at bed time, for a month. The subjects were instructed to first wash their face with warm water and soap thoroughly to remove any sweat, dirt, and oils from their faces. They were instructed apply the stabilized Botulinum toxin cream or placebo cream around their eyes, forehead, and neck or on the wrinkled skin areas with the supplied applicator so as to avoid any contamination of the product by hand. All subjects were examined prior to the beginning of the study by a qualified dermatologist and were declared healthy and fit to enter in the study. They were photographed prior to the beginning of the study. All subjects were asked to follow their normal daily routine without any restriction and asked to live their normal life style.

The primary efficacy measurements were the investigator's rating of glabellar line severity at maximum frown at Day 30 post-treatment and the subject's global assessment of change in appearance of glabellar lines at Day 30 post-treatment. For the investigator rating, a photoguide was provided to each study center to assist in grading the severity of glabellar lines using a 4-point grading scale (0=none 1=mild 2=moderate 3=severe). A responder was defined as having a severity grade of 0 or 1. For the global assessment of change in appearance of glabellar lines, the subject responded to the question, "How would you rate the change in the appearance of your glabellar lines compared with immediately before your treatment with the non-invasive Botulinum toxin cream?" The ratings of responses by subjects were from +4 (complete improvement, about 100%) to −4 (very marked worsening, about 100% worse or greater). A responder was defined as having a grade of at least +2 (moderate improvement, about 50%).

A secondary efficacy endpoint was the investigator's rating of glabellar line severity at rest at Day 30 post-treatment in those subjects who at baseline demonstrated a glabellar line severity score at rest of moderate or severe. For the investigators rating, the criteria for effectiveness was a 30 percentage point difference between the stabilized Botulinum toxin cream and placebo treatment groups in the incidence of subjects with an investigator's rating of glabellar line severity of none or mild at maximum frown. For the subjects rating, the criteria for effectiveness was a 25 percentage point difference between the stabilized Botulinum toxin cream and placebo treatment groups in the incidence of subjects with a score of at least +2 (moderate improvement) in subject's global assessment of change in the appearance of glabellar lines.

The combined results are shown in Table 1 below. There were 40 subjects (20 subjects in the Botulinum toxin cream treated group and 20 subjects in the placebo cream treated group) who had glabellar line severity scores at rest of moderate or severe.

The mean age was 54 years, with a range of 40 to 74 years. Of this, majorities were ≦50 years of age and 6.0% were ≧65 years of age. Most of the subjects were female, 80% (32/40) and Caucasian, 83.8%.

In these studies, the severity of glabellar lines was reduced in less than 7 days in the Botulinum toxin cream group compared to the placebo cream group as measured both by investigator rating of glabellar line severity at maximum frown and at rest, and by subject's global assessment of change in appearance of glabellar lines. By Day 10, 80% (16/20) of subjects had achieved a severity score of mild at maximum frown by the investigator's assessment. This increased to 92% by the primary efficacy endpoint day of Day 30, compared to placebo-treated patients (Table 1). By Day 10, 84% of subjects in the active group assessed moderate or better improvement in their own appearance (+2 or better). This increased to 93% by the primary efficacy endpoint day of Day 30, compared to 3% of placebo-treated patients. Based on resting appearance as judged by the investigator, 62% of subjects achieved a severity score of none or mild at Day 11, and 94% by the efficacy endpoint day of Day 30.

TABLE I

| Day | Botox-Cream | Placebo | Difference | p-Value |
|---|---|---|---|---|
| 7 | 76% (15/20) | 3% (1/20) | 73% | <0.0001 |
| 10 | 80% (16/20) | 3% (1/20) | 77% | <0.0001 |
| 20 | 88% (18/20) | 5% (1/20) | 83% | <0.0001 |
| 30 | 94% (19/20) | 5% (1/20) | 89% | <0.0001 |

Exemplary results can be seen in the before and after photographs of FIGS. 3A to 3D.

Example 6

Hyaluronic Acid Delivery System

In a round bottom flask of 50 mL capacity, 10 mg of soluble collagen, 10 mg of elastin were weighed. The mixture was solubilized in 10 mL of sterile saline solution (0.9%). The mixture was stirred continuously. In a separate 50 mL round bottom flask, 25 mg of sphingosine and 25 mg cerebroside (or 20 mg phosphatidyl choline+25 mg phosphatidy serine) were combined and the mixture was dissolved in pure ethanol or in a mixture of 70:30 isoproanol:ethanol. The alcohol was completely removed by rotary vacuum evaporation to obtain a uniform coating of the phospholipids mixture on the flask wall. 500 mg hyaluronic acid or Na hyaluronate solution in 50 ml of (0.9%) saline was added. The flask was swirled and then stirred continuously for several minutes at room temperature. The hyaluronic acid was thus coated uniformly with the phospholipid micelle coating. This coated and preserved micellar hyaluronic acid solution was then added to the flask containing the mixture of collagen and cross linked lowed molecular weight elastin. The solution was stirred for about 5 minutes slowly and then kept at a room temperature in a brown glass vial.

Example 7

Preparation of a Cream Containing Encapsulated HA

The following components were used to prepare a cream for topical application:

| Phase A: | |
|---|---|
| De-ionized Water | 74.7% |
| Tetra Sodium EDTA | 0.3-0.5% |
| Methyl Paraben | 0.2% |
| Propylene Glycol | 2.0-3.0% |
| Alpha Hydroxyacid (fruit acid) | 1.0-2.0% |
| (Total 78.2%) | |
| Phase B: | |
| Cetyl Alcohol (Adol 52 NF) | 1.0-2.0% |
| Cetearyl Alcohol | 1.0-2.0% |
| Glyceryl Stearate | 1.0-2.0% |
| PEG-100 Stearate | 1-2% |
| Stearic Acid (Emersol 132) | 4.5% |
| Sorbitan Palmitate | 0.5-0.7% |
| Polysorbate-85 | 0.5-1.0% |
| HoHoba Oil | 2-5% |
| Lanolin | 1-2% |
| Tocopheryl Acetate | 0.3-0.5% |
| Dimethicone 200 | 0.5-0.7% |
| BHA | 0.1% |
| Propylparaben | 0.1% |
| Diazolidinyl UREA | 0.2% |
| (Total 13.7%) | |
| Phase C: | |
| Fragrance (lilac, jasmine) | as needed |
| Aloe Vera (powder) | 0.5-1.0% |
| Retinyl A (pure) | 0.03-0.05% |
| Hyaluronic Acid (micelle) | 1.0-1.5% |
| Collagen + Elastin | 1.0-1.5% |
| Talcum Powder (Ti02) | 0.1-0.3% |
| (Total 2.63%) | |
| Phase D (absorption enhancers): | |
| d-limonene | 0.7% |
| Allantoin | 0.5% |
| Fulvic Acid | 0.5% |
| Quillaja saponaria (QTS) | 0.3% |
| Myrrh Extract | 0.2% |
| Glyquin (whitening agent) | 3.5-4.0% |
| (Total 5.5%) | |

Example 8

Clinical Studies with the HA Cream

This study was done under the supervision of a dermatologist/plastic surgeon. The subjects were pre-scanned and were declared healthy. They were given a vial of the hyaluronic acid cream and instructed apply it once in the evening time for 30 days. The subjects were instructed to remove their make-up and asked to wash their face with warm water and soap or cleanser. Subjects were asked to apply the cream with the given applicator on the wrinkled area of their face and neck. All subjects were photographed before and after to evaluate the effect at, the end of the 30 days period. Exemplary results can be seen in the photographs shown in FIG. 4.

What is claimed is:

1. A stabilized protein composition for topical transdermal delivery of an active agent said composition comprising collagen, elastin, one or more absorption enhancers selected from a group consisting of short chain alcohols, long chain alcohols, polyalcohols, amines, amides, urea, amino acids or their esters, pyrrolidones, derivatives of pyrrolidones, terpenes, derivatives of terpenes, fatty acids and their esters, macrocyclic compounds, tensides, sulfoxides, liposomes, transfersomes, lecithin vesicles, ethosomes, water surfactants polyols, and essential oils wherein said active agent encapsulated in a micelle formed by the combination of surfactants, solvents and stabilizers and wherein said protein composition is stabile at room temperature of between 15 and 25 degrees C. for a period of at least two weeks.

2. A composition according to claim 1 wherein the absorption enhancer is selected from the group consisting of d-limonene, allantoin, fulvic acid, myrrh, hydroquinone glyquin, quillaja saponaria (QTS), and acanthophyllum squarrusom (ATS).

3. A composition according to claim 2, wherein the active agent is selected from the group consisting of a paralysing agent, hyaluronic acid, antioxidants, hormones, growth factors, vaccine agents, drugs, vasodilators, therapeutic proteins, small molecules, amines, peroxides, antiperspirant agents, analgesics, and combinations thereof.

4. A composition according to claim 3, wherein the paralysing agent is botulinum toxin.

5. A composition according to claim 1, wherein the active agent is hyaluronic acid.

6. A composition according to claim 1, comprising both botulinum toxin and hyaluronic acid.

7. A composition according to claim 1 formulated in a format selected from the group consisting of a cream, a lotion, spray, an ointment, a gel, a powdered mask, a paste, cleanser, and a foundation.

8. A composition according to claim 7 comprising an additive selected from the group consisting of a perfume, colorant, thickening agent, vegetable oil, emulsifier, solvent, pH adjusting agent, antiseptic agent, preservative, vitamin, sunblock, surfactants and combinations thereof.

9. A composition according to claim 1, comprising:
  i. Approximately 1 to 40% w/w/ collagen;
  ii. Approximately 1 to 40% w/w elastin;
  iii. Approximately 0.1 to 15% sphingosine phospholipid; and
  iv. Approximately 0.1 to 15% cerebroside phospholipid.

10. A method for making a stabilized active agent composition, said method comprising the steps of: i. Dissolving a phospholipid in a solvent to prepare a phospholipid solution; and ii. admixing the phospholipid solution with an active agent so as provide a phospholipid micelle encapsulated active agent solution.

11. A method according to claim 10, further comprising the step of: i. combining the micelle solution with a solution of solubilized collagen and elastin.

12. The method of claim 10, wherein the phospholipid is selected from the group consisting of sphingosine, cerebroside and combinations thereof.

13. The method of claim 12, wherein, sphingosine and cerebroside are used in equal amounts.

14. The method of claim 10, wherein the solvent is an alcohol.

15. The method of claim 14, wherein the alcohol is selected from the group consisting of isopropanol, ethanol and mixtures thereof.

16. The method of claim 11, wherein the solution of solubilized collagen and elastin comprises equal amounts of collagen and elastin.

17. The method of claim 10, wherein the active agent is selected from the group consisting of botulinum toxin, hyaluronic acid, Vitamin A, Vitamin C, Vitamin E, Zinc, Selenium, lycopene, N-Acetyl-Cysteine, natural plant extracts of Grape Skin, Bilberry and Green Tea, vasodilators, hormones, growth factors, vaccine agents, drugs, therapeutic proteins, small molecules, antiperspirant agents, analgesics and combinations thereof.

18. The method of claim 17, wherein the active agent is hyaluronic acid and/or botulinum toxin.

19. The method of claim 10, further comprising the step of adding a permeation enhancing compound selected from the group consisting of d-limonene, allantoin, fulvic acid, myrrh, hydroquinone, glyquin, quillaja saponaria, and acanthophyllum squarrusom.

20. The method of claim 12, wherein the concentration of sphingosine is about 0.1 to 15 wt/wt % and the concentration of cerebroside is about 0.1 to 15 wt/wt %.

21. A method of treating damaged skin by topically applying the composition as defined in claim 4 to the damaged skin.

22. A method of treating damaged skin by topically applying the composition as defined in claim 5 to the damaged skin.

* * * * *